US012635855B2

(12) United States Patent
Niwa

(10) Patent No.: US 12,635,855 B2
(45) Date of Patent: May 26, 2026

(54) MEDICAL DETECTION ATTACHMENT AND MEDICAL ENDOSCOPE SYSTEM

(71) Applicant: Sony Olympus Medical Solutions Inc., Tokyo (JP)

(72) Inventor: Yoshiaki Niwa, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 497 days.

(21) Appl. No.: 18/177,755

(22) Filed: Mar. 3, 2023

(65) Prior Publication Data

US 2023/0284880 A1 Sep. 14, 2023

(30) Foreign Application Priority Data

Mar. 11, 2022 (JP) ................................. 2022-038567

(51) Int. Cl.
*A61B 1/00* (2006.01)
*A61B 1/06* (2006.01)
*A61B 1/07* (2006.01)

(52) U.S. Cl.
CPC ...... *A61B 1/00131* (2013.01); *A61B 1/00016* (2013.01); *A61B 1/00027* (2013.01); *A61B 1/00126* (2013.01); *A61B 1/063* (2013.01); *A61B 1/0655* (2022.02); *A61B 1/0669* (2013.01); *A61B 1/07* (2013.01)

(58) Field of Classification Search
CPC ........... A61B 1/00016; A61B 1/00027; A61B 1/00126; A61B 1/00131; A61B 1/063; A61B 1/0655; A61B 1/0669; A61B 1/07;

A61B 1/00112; A61B 1/00117; A61B 1/00121; A61B 2017/00477; A61B 2018/00172; A61B 2018/00178;
(Continued)

(56) References Cited

U.S. PATENT DOCUMENTS 6,090,123 A * 7/2000 Culp ................ A61B 17/32002
606/180
6,689,050 B1 * 2/2004 Beutter .................. A61B 1/045
600/117
(Continued)

FOREIGN PATENT DOCUMENTS

JP H05183224 A 7/1993
JP 2007014423 A 1/2007
(Continued)

OTHER PUBLICATIONS

"Part 11: Wireless LAN Medium Access Control (MAC) and Physical Layer (PHY) Specifications Amendment Enhancements for High Efficiency WLAN", IEEE P802.11ax/D6.0, Nov. 2019, pp. 508-511.
(Continued)

*Primary Examiner* — Aaron B Fairchild
(74) *Attorney, Agent, or Firm* — XSENSUS LLP

(57) ABSTRACT

A medical detection attachment includes: an attachment body attached to a connection portion between a light guide configured to guide a laser beam and a rigid endoscope configured to irradiate a subject with the laser beam via the light guide; a first detector provided in the attachment body and configured to detect connection between the attachment body and the rigid endoscope; and a second detector provided in the attachment body and configured to detect connection between the attachment body and the light guide.

14 Claims, 7 Drawing Sheets

(58) Field of Classification Search
CPC .......... A61B 2562/22; A61B 2562/225; A61B
2562/227; A61B 2562/228
See application file for complete search history.

(56) References Cited

U.S. PATENT DOCUMENTS

| | | | | |
|---|---|---|---|---|
| 2005/0014996 A1* | 1/2005 | Konomura | ......... | G02B 23/2476 |
| | | | | 600/118 |
| 2008/0147089 A1* | 6/2008 | Loh | ......... | A61B 34/71 |
| | | | | 606/130 |
| 2018/0228557 A1* | 8/2018 | Darisse | ......... | A61B 1/0057 |

FOREIGN PATENT DOCUMENTS

| | | | |
|---|---|---|---|
| JP | 2013149484 A | 8/2013 |
| JP | 2015132741 A | 7/2015 |
| JP | 2017125874 A | 7/2017 |
| WO | WO-2020175625 A1 | 9/2020 |

OTHER PUBLICATIONS

"Part 11: Wireless LAN Medium Access Control (MAC) and Physical Layer (PHY) Specifications", IEEE P802.11be™/ D1.0, IEEE Computer Society, May 2021, pp. 1-635.

* cited by examiner

MEDICAL DETECTION ATTACHMENT AND MEDICAL ENDOSCOPE SYSTEM

CROSS-REFERENCE TO RELATED APPLICATION

This application claims priority from Japanese Application No. 2022-038567, filed on Mar. 11, 2022, the contents of which are incorporated by reference herein in its entirety.

BACKGROUND

The present disclosure relates to a medical detection attachment and a medical endoscope system.

In recent years, in a medical endoscope system that observes a subject, a laser beam having a narrow band and high coherence may be used as light for observing the corresponding subject.

Such a medical endoscope system includes a rigid endoscope, a light guide, and a light source device described below.

The light source device projects a laser beam.

The light guide connects the rigid endoscope and the light source device and guides the laser beam projected from the corresponding light source device to the rigid endoscope.

The rigid endoscope is inserted into the subject and irradiates the inside of the subject with the laser beam guided by the light guide from the distal end. In addition, the rigid endoscope captures a subject image inside the corresponding subject.

Here, the light guide may be easily removed from the rigid endoscope without using a tool. That is, when the light guide is detached from the rigid endoscope, it is concerned that the user is irradiated with the laser beam projected from the projection end of the corresponding light guide. In order to ensure safety, it is required to design the laser beam projected from the projection end of the light guide so as to satisfy the requirement defined in the laser standard indicating the "safety standard of the laser product". In such a design, the light amount of the laser beam projected from the projection end of the light guide is limited by the corresponding laser standard, and as a result, it is difficult to ensure the light amount of the laser beam projected from the distal end of the rigid endoscope.

In addition, in the related art, there is proposed a medical endoscope system that projects a laser beam from a light source device only when connection between a light guide and a rigid endoscope is detected (for example, see U.S. Pat. No. 7,018,331).

In the medical endoscope system disclosed in U.S. Pat. No. 7,018,331, connection between the light guide and the rigid endoscope is detected by using a detection attachment in which an object to be detected such as a radio frequency identifier (RFID) tag is built.

Specifically, the light guide includes a detector that detects an object to be detected described above. Then, by connecting the detection attachment to the rigid endoscope and connecting the corresponding light guide to the detection attachment, the object to be detected built in the corresponding detection attachment is detected by using the detector provided in the light guide. As a result, it is detected that the light guide and the rigid endoscope are connected.

If the laser beam is projected from the light source device only when the light guide and the rigid endoscope are connected, when the corresponding light guide is detached from the corresponding rigid endoscope, the corresponding laser beam is not projected from the projection end of the corresponding light guide. That is, such a configuration may be designed so that the laser beam projected from the distal end of the rigid endoscope satisfies the requirement defined in the laser standard indicating the "safety standard of the laser product". Then, when designed in this way, the light amount of the laser beam projected from the projection end of the light guide may be set to a high light amount without being limited by the corresponding laser standard, and as a result, the light amount of the laser beam projected from the distal end of the rigid endoscope may be ensured.

SUMMARY

However, the medical endoscope system disclosed in U.S. Pat. No. 7,018,331 has the following problems when the connection procedure of the detection attachment is wrong.

That is, when the detection attachment is first connected to the light guide, it is detected that the corresponding light guide and the corresponding rigid endoscope are connected even though the light guide and the rigid endoscope are not connected. As a result, the laser beam is projected from the projection end of the corresponding light guide even though the light guide and the rigid endoscope are not connected. That is, safety may not be ensured.

Therefore, there is a demand for a technique capable of ensuring the light amount of the laser beam projected to the subject while securing safety.

According to one aspect of the present disclosure, there is provided a medical detection attachment including: an attachment body attached to a connection portion between a light guide configured to guide a laser beam and a rigid endoscope configured to irradiate a subject with the laser beam via the light guide; a first detector provided in the attachment body and configured to detect connection between the attachment body and the rigid endoscope; and a second detector provided in the attachment body and configured to detect connection between the attachment body and the light guide.

DETAILED DESCRIPTION

Figure 1:
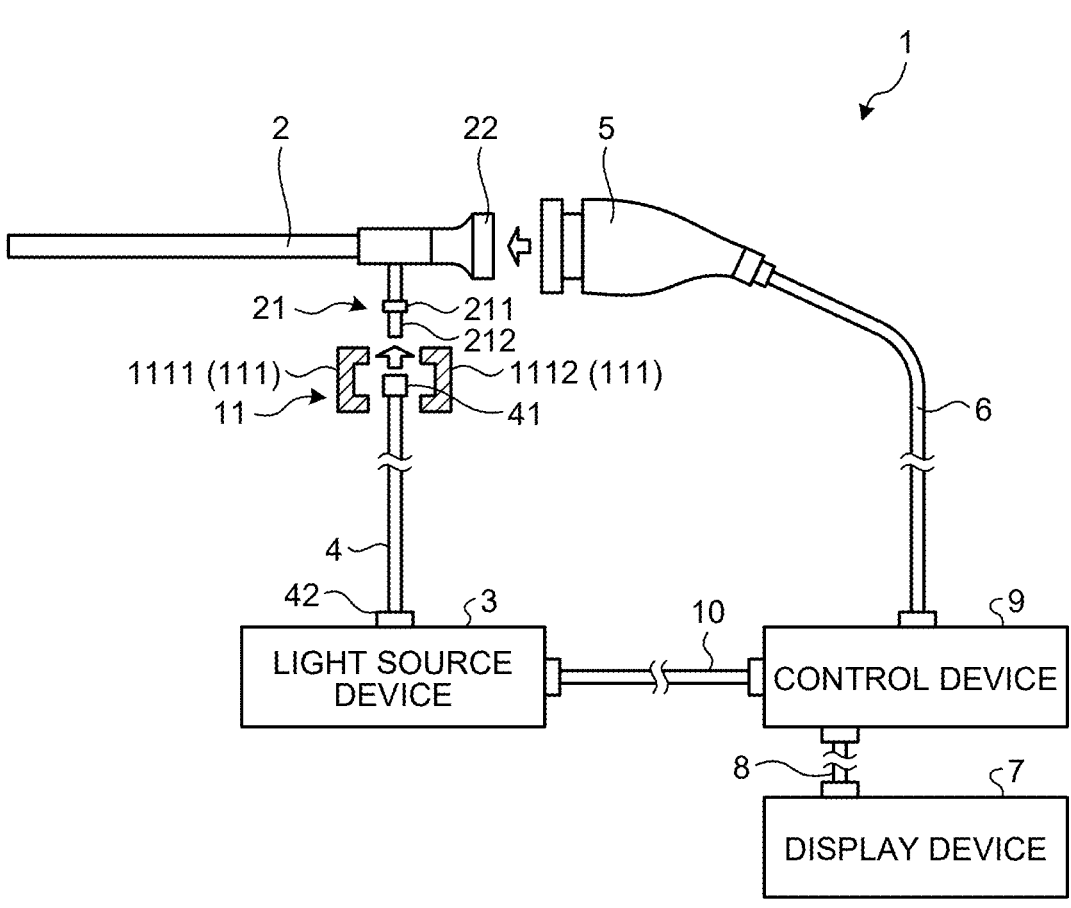
FIG. 1 is a diagram illustrating a medical endoscope system according to a first embodiment.

Hereinafter, modes for carrying out the present disclosure (embodiments) are described with reference to the drawings. Note that the present disclosure is not limited by the embodiments described below. Furthermore, in the description of the drawings, the same portions are denoted by the same reference numerals.

First Embodiment

Schematic Configuration of Medical Endoscope System

FIG. 1 is a diagram illustrating a medical endoscope system 1 according to a first embodiment.

The medical endoscope system 1 is a system that is used in the medical field and observes a subject (in vivo). As illustrated in FIG. 1, the medical endoscope system 1 includes an insertion unit 2, a light source device 3, a light guide 4, a camera head 5, a first transmission cable 6, a display device 7, a second transmission cable 8, a control device 9, a third transmission cable 10, and a detection attachment 11.

The insertion unit 2 corresponds to a rigid endoscope according to the present disclosure, has an elongated shape that is entirely rigid or partially soft and partially rigid, and is inserted into a living body.

An optical system (not illustrated) configured by using one or a plurality of lenses and configured to collect a subject image is provided in the insertion unit 2.

As illustrated in FIG. 1, the insertion unit 2 includes an insertion unit side connector 21 to which a first light guide side connector 41 of the light guide 4 is detachably connected.

Note that the configuration of the insertion unit side connector 21 is described in "Configurations of Insertion Unit Side Connector and First Light Guide Side Connector" described below.

The light source device 3 is connected to a second light guide side connector 42 of the light guide 4 and supplies light (normal light such as white light or excitation light (laser beam)) designated by the corresponding control device 9 to the incident end of the corresponding light guide 4 under the control of the control device 9. In the first embodiment, the light source device 3 is configured separately from the control device 9, but the present disclosure is not limited thereto, and a configuration provided in the corresponding control device 9 may be employed.

Note that a detailed configuration of the light source device 3 is described in "Configuration of Light Source Device" described below.

In the light guide 4, the first light guide side connector 41 on the incident end side is detachably connected to the insertion unit side connector 21, and also the second light guide side connector 42 on the projection end side is detachably connected to a light source device side connector 30 (see FIG. 2) of the light source device 3. Then, the light guide 4 supplies the light (normal light such as white light or excitation light (laser beam)) supplied from the light source device 3 to the insertion unit 2. The light supplied to the insertion unit 2 is emitted into a living body from the distal end of the corresponding insertion unit 2. Normal light or excitation light (laser beam) reflected in a living body, and fluorescence emitted from a fluorescent substance by exciting the corresponding fluorescent substance in the corresponding living body by the excitation light are collected by the optical system in the insertion unit 2.

The configuration of the first light guide side connector 41 is described in "Configuration of Insertion Unit Side Connector and First Light Guide Side Connector" described below.

The camera head 5 is detachably connected to an eyepiece portion 22 in the insertion unit 2. Then, under the control of the control device 9, the camera head 5 images a subject image collected by the insertion unit 2 and generates an image signal (hereinafter, referred to as a captured image).

One end of the first transmission cable 6 is detachably connected to the control device 9, and the other end is detachably connected to the camera head 5. Then, the first transmission cable 6 transmits a captured image and the like output from the camera head 5 to the control device 9 and also transmits a control signal, a synchronization signal, a clock, power, and the like output from the control device 9 to the camera head 5.

Note that, the transmission of the captured image and the like from the camera head 5 to the control device 9 via the first transmission cable 6 may be transmission of the corresponding captured image and the like by an optical signal or may be transmission by an electric signal. The same applies to transmission of the control signal, the synchronization signal, and the clock from the control device 9 to the camera head 5 via the first transmission cable 6.

The display device 7 is configured with a display by using liquid crystal, organic electro luminescence (EL), or the like and displays an image based on a video signal from the control device 9 under the control of the corresponding control device 9.

One end of the second transmission cable 8 is detachably connected to the display device 7, and the other end is detachably connected to the control device 9. Then, the second transmission cable 8 transmits a video signal processed by the control device 9 to the display device 7.

The control device 9 is configured with a central processing unit (CPU), a field-programmable gate array (FPGA), and the like and integrally controls operations of the light source device 3, the camera head 5, and the display device 7. For example, the control device 9 outputs a control signal to the light source device 3 according to an observation mode such as a normal observation mode or a fluorescence observation mode and causes light (normal light such as white light or excitation light (laser beam)) corresponding to the corresponding observation mode to be projected from the light source device 3. Furthermore, the control device 9 executes various image processes on the captured image output from the camera head 5 and generates a video signal for displaying the corresponding captured image. Then, the control device 9 outputs the corresponding video signal to the display device 7 via the second transmission cable 8 to display the captured image based on the video signal on the display device 7.

One end of the third transmission cable 10 is detachably connected to the light source device 3, and the other end is detachably connected to the control device 9. Then, the third transmission cable 10 transmits the control signal from the control device 9 to the light source device 3.

The detection attachment 11 is an attachment for detecting a connection state between the light guide 4 and the insertion unit 2 and corresponds to a medical detection attachment according to the present disclosure.

Note that a detailed configuration of the detection attachment 11 is described in "Configuration of Detection Attachment" described below.

Configuration of Light Source Device

Figure 2:
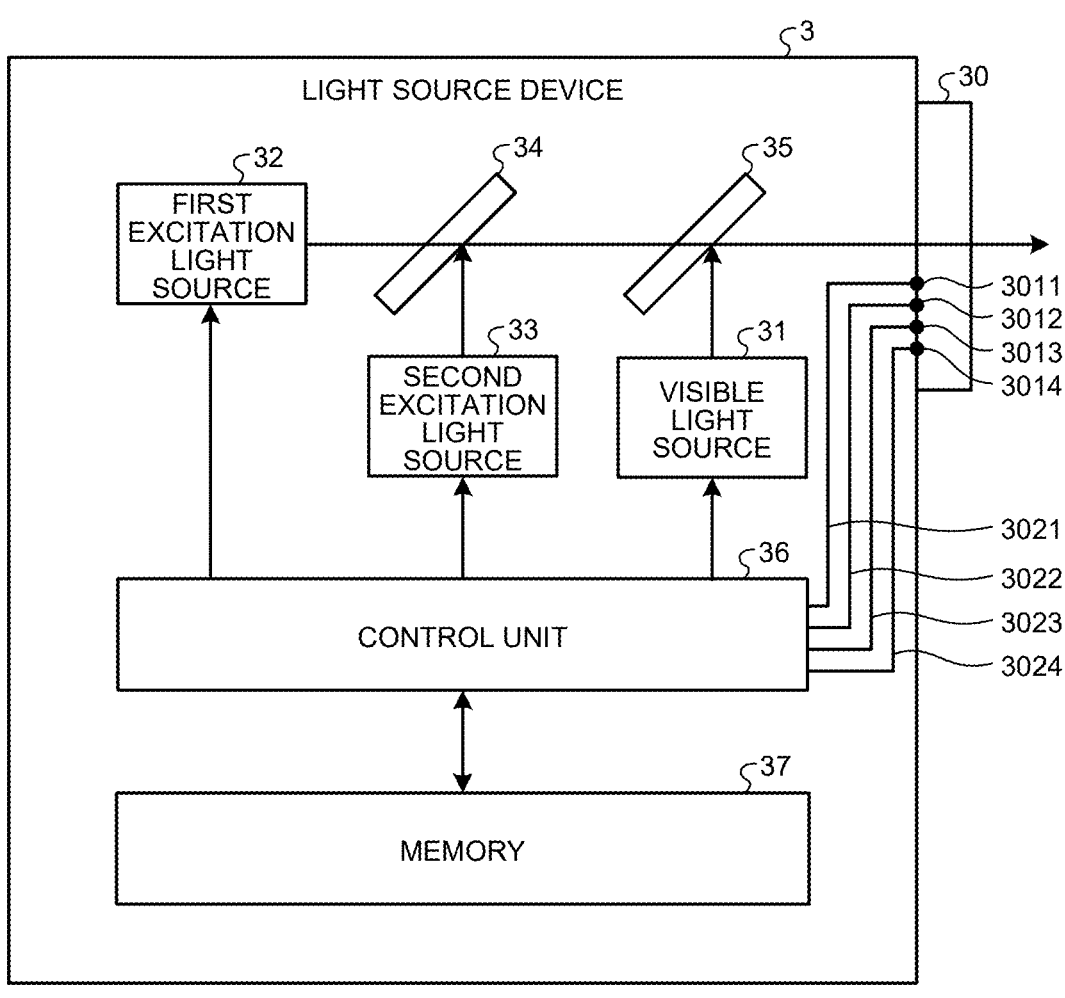
FIG. 2 is a block diagram illustrating a configuration of a light source device.

FIG. 2 is a block diagram illustrating a configuration of the light source device 3.

Next, the configuration of the light source device 3 is described with reference to FIG. 2.

As illustrated in FIG. 2, the light source device 3 includes a visible light source 31, first and second excitation light sources 32 and 33, first and second dichroic mirrors 34 and 35, a control unit 36, and a memory 37.

The visible light source 31 is a light source used in both the normal observation mode and the fluorescence observation mode and projects (emits) normal light such as white light in a visible wavelength band. In the first embodiment, the visible light source 31 is configured with a light emitting diode (LED) that emits white light (normal light).

The first excitation light source 32 corresponds to a laser beam source device according to the present disclosure. The first excitation light source 32 is a light source used in the fluorescence observation mode and is configured with a semiconductor laser that emits excitation light (hereinafter, referred to as a first laser beam) having a peak wavelength of about 405 nm. The first laser beam is excitation light that excites protoporphyrin that is taken into cells after administration of 5-aminolevulinic acid (5-ALA) into a subject and biosynthesized in mitochondria. When excited by the first laser beam, the corresponding protoporphyrin emits fluorescence having peak wavelengths of about 636 nm and about 705 nm, respectively.

The second excitation light source 33 corresponds to a laser beam source device according to the present disclosure. The second excitation light source 33 is a light source used in the fluorescence observation mode and is configured with a semiconductor laser that emits excitation light in a near-infrared wavelength band (peak wavelength: about 808 nm) (hereinafter, referred to as a second laser beam). The second laser beam is excitation light that excites indocyanine green (fluorescent substance). When excited by the second laser beam, the indocyanine green emits fluorescence having a longer peak wavelength (about 835 nm) on a wavelength side than the peak wavelength of the corresponding second laser beam.

In the first embodiment, light (normal light and first and second laser beams) projected from the visible light source 31 and the first and second excitation light sources 32 and 33 is designed to be in a class (Laser Standard (for example, IEC 60825-1: 2014 or 2007) indicating "safety standard of the laser product") shown in Tables 1 and 2 below.

TABLE 1

| | Light emitted at the same time | | | |
| | Normal light | First laser beam | Second laser beam | None |
|---|---|---|---|---|
| Normal light | — | Class 3R | Class 1 | — |
| First laser beam | Class 3R | — | Class 1 | Class 3R |
| Second laser beam | Class 1 | Class 1 | — | Class 1 |

TABLE 2

| | Light emitted at the same time | | | |
| | Normal light | First laser beam | Second laser beam | None |
|---|---|---|---|---|
| Normal light | — | Class 3R | Class 3R | — |
| First laser beam | Class 3R | — | Class 3R | Class 3R |
| Second laser beam | Class 3R | Class 3R | — | Class 3R |

Here, Table 1 shows classes of light projected from the "distal end of the insertion unit 2". For example, as shown in Table 1, when the normal light and the second laser beam are simultaneously emitted, the corresponding second laser beam is designed to be in Class 1. For example, when the first and second laser beams are simultaneously emitted, the corresponding first and second laser beams are designed to be in Class 1. Furthermore, for example, when only the second laser beam is emitted, the corresponding second laser beam is designed to be in Class 1.

In addition, Table 2 shows classes of light projected from the "projection end of the light guide 4". For example, as shown in Table 2, when the normal light and the second laser beam are simultaneously emitted, the corresponding second laser beam is designed to be in Class 3R. For example, when the first and second laser beams are simultaneously emitted, the corresponding first and second laser beams are designed to be in Class 3R. Furthermore, for example, when only the second laser beam is emitted, the corresponding second laser beam is designed to be in Class 3R.

The first dichroic mirror 34 is a dichroic mirror that transmits the first laser beam and also reflects the second laser beam in the same direction as the traveling direction of corresponding the first laser beam.

The second dichroic mirror 35 is a dichroic mirror that transmits the first and second laser beams and reflects normal light in the same direction as the traveling direction of the corresponding first and second laser beams.

The control unit 36 is implemented by executing various programs stored in the memory 37 by a controller such as a CPU or a micro processing unit (MPU) and controls the entire operation of the light source device 3. Note that the control unit 36 is not limited to the CPU or the MPU and may be configured with an integrated circuit such as an application specific integrated circuit (ASIC) or an FPGA.

Then, the control unit 36 drives a light source designated by the control device 9 among the visible light source 31 and the first and second excitation light sources 32 and 33 according to a control signal output from the corresponding control device 9. At this time, the control unit 36 executes specific lighting drive control.

Note that details of the lighting drive control are described in "Operation of Control Unit" described below.

The memory 37 stores a program executed by the control unit 36, information necessary for processing of the corresponding control unit 36, and the like.

Figure 3:
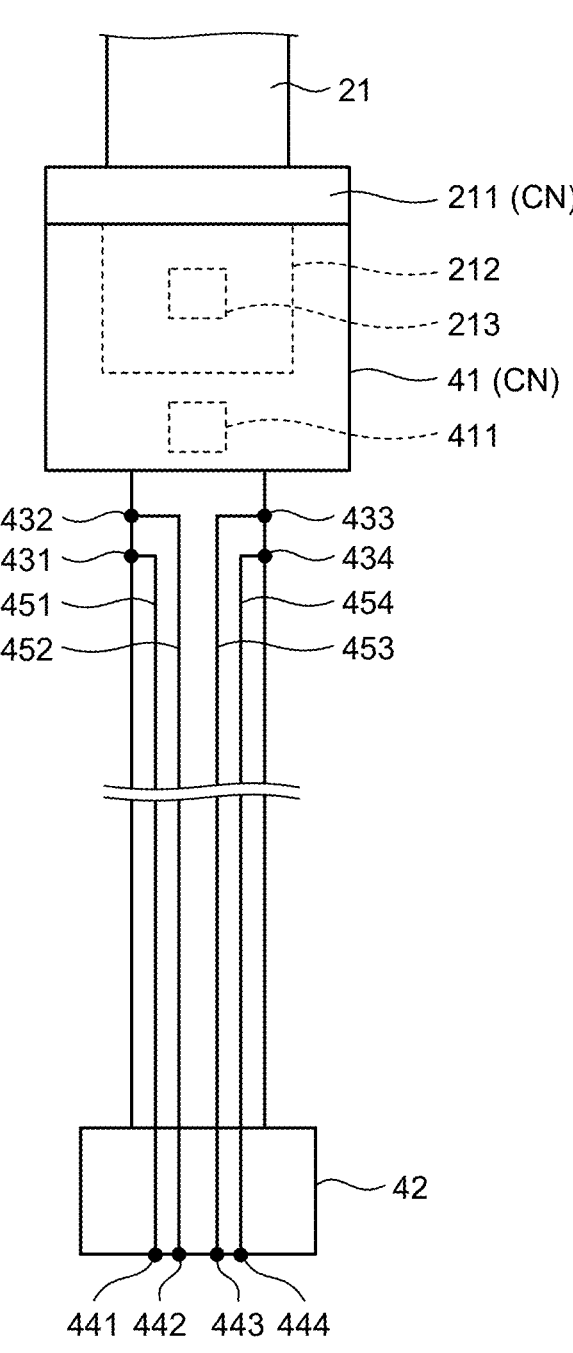
FIG. 3 is a view illustrating a configuration of an insertion unit side connector and a first light guide side connector.

Configurations of Insertion Unit Side Connector and First Light Guide Side Connector FIG. 3 is a view illustrating a configuration of the insertion unit side connector 21 and the first light guide side connector 41.

Next, configurations of the insertion unit side connector 21 and the first light guide side connector 41 are described with reference to FIG. 3.

The insertion unit side connector 21 has a substantially cylindrical shape as a whole protruding in a direction (vertical direction in FIG. 3) orthogonal to the longitudinal direction of the insertion unit 2.

In the insertion unit side connector 21, a flange portion 211 (FIG. 3) having a larger outer diameter dimension than the other portions is provided on an outer peripheral surface of a substantially central portion in the protruding direction.

Then, in a state in which the first light guide side connector 41 is connected, as illustrated in FIG. 3, the insertion unit side connector 21 is in a state in which a portion on the distal end side of the flange portion 211 (hereinafter, referred to as a distal end portion 212) is inserted into the first light guide side connector 41, and also the corresponding flange portion 211 abuts on the corresponding first light guide side connector 41.

Here, as illustrated in FIG. 3, a first integrated circuit (IC) tag 213 is built in the distal end portion 212. In the first embodiment, the first IC tag 213 is configured with a known RFID tag. That is, though not specifically illustrated, the first IC tag 213 includes an antenna and an IC chip. Then, the IC chip operates by using radio waves received from a first IC detector 112 described below via the corresponding antenna as a power source and transmits data recorded in the corresponding IC chip to the first IC detector 112 via the corresponding antenna.

The first light guide side connector 41 has a cylindrical shape having substantially the same outer diameter dimension as the flange portion 211.

Here, as illustrated in FIG. 3, a second IC tag 411 is built in the first light guide side connector 41. In the first embodiment, the second IC tag 411 is configured with a known RFID tag, like the first IC tag 213. That is, though not specifically illustrated, the second IC tag 411 includes an antenna and an IC chip. Then, the corresponding IC chip operates by using radio waves received from a second IC detector 113 described below via the corresponding antenna as a power source and transmits data recorded in the corresponding IC chip to the corresponding second IC detector 113 via the corresponding antenna.

Figure 4:
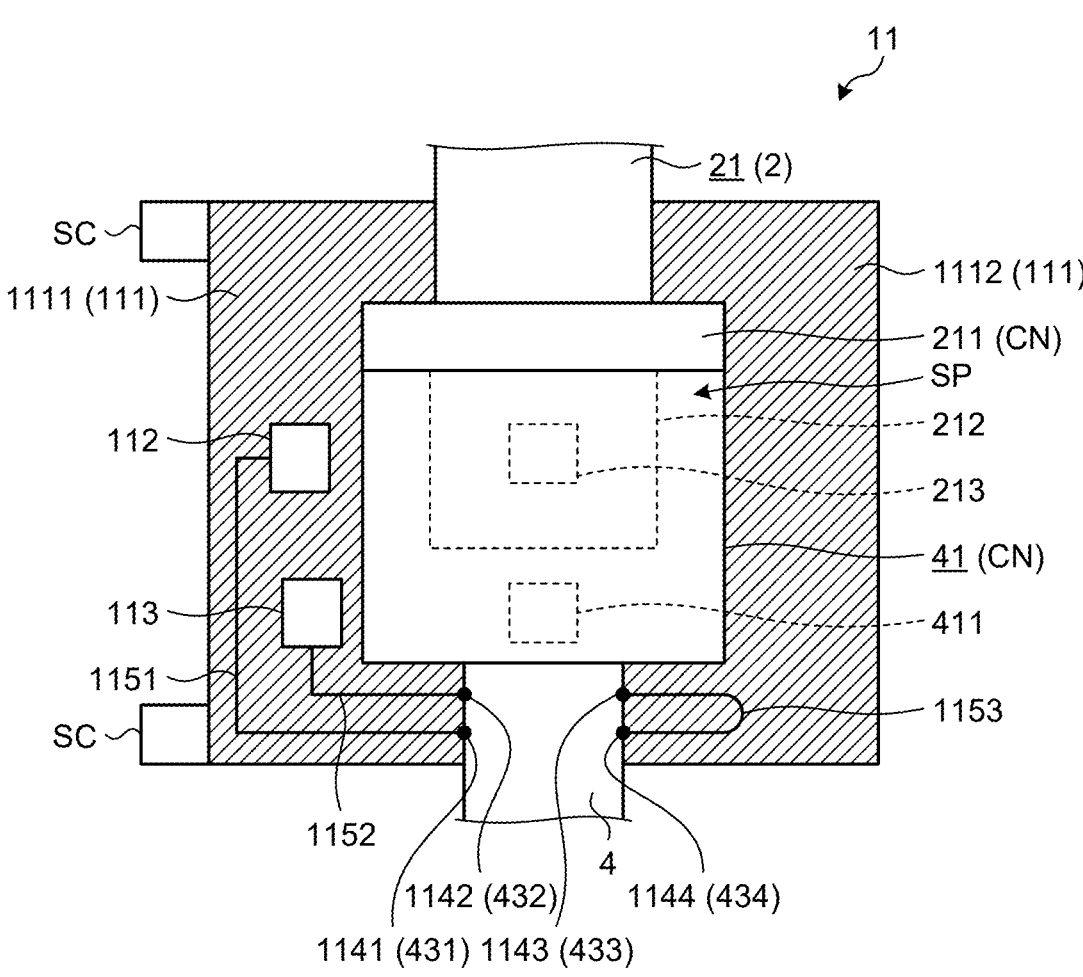
FIG. 4 is a diagram illustrating a configuration of a detection attachment.

In the light guide 4, as illustrated in FIGS. 3 and 4, first to fourth one end side contact points 431 to 434 are provided on the outer surface of the first light guide side connector 41. Similarly, the second light guide side connector 42 includes first to fourth other end side contact points 441 to 444. The first one end side contact point 431 and the first other end side contact point 441 are electrically connected by a first light guide side wiring 451 tracing the inside of the light guide 4. In addition, the second one end side contact point 432 and the second other end side contact point 442 are electrically connected by a second light guide side wiring 452 tracing the inside of the light guide 4. Further, the third one end side contact point 433 and the third other end side contact point 443 are electrically connected by a third light guide side wiring 453 tracing the inside of the light guide 4. In addition, the fourth one end side contact point 434 and the fourth other end side contact point 444 are electrically connected by a fourth light guide side wiring 454 tracing the inside of the light guide 4.

Here, as illustrated in FIG. 2, the light source device side connector 30 includes first to fourth light source device side contact points 3011 to 3014.

When the second light guide side connector 42 is connected to the light source device side connector 30, the first light source device side contact point 3011 is electrically connected to the first other end side contact point 441. In addition, the first light source device side contact point 3011 is electrically connected to the control unit 36 by a first light source device side wiring 3021 (FIG. 2).

When the second light guide side connector 42 is connected to the light source device side connector 30, the second light source device side contact point 3012 is electrically connected to the second other end side contact point 442. In addition, the second light source device side contact point 3012 is electrically connected to the control unit 36 by a second light source device side wiring 3022 (FIG. 2).

When the second light guide side connector 42 is connected to the light source device side connector 30, the third light source device side contact point 3013 is electrically connected to the third other end side contact point 443. In addition, the third light source device side contact point 3013 is electrically connected to the control unit 36 by a third light source device side wiring 3023 (FIG. 2).

When the second light guide side connector 42 is connected to the light source device side connector 30, the fourth light source device side contact point 3014 is electrically connected to the fourth other end side contact point 444. In addition, the fourth light source device side contact point 3014 is electrically connected to the control unit 36 by a fourth light source device side wiring 3024 (FIG. 2).

Configuration of Detection Attachment

FIG. 4 is a diagram illustrating a configuration of the detection attachment 11.

Next, a configuration of the detection attachment 11 is described with reference to FIG. 4.

As illustrated in FIG. 4, the detection attachment 11 includes an attachment body 111 and the first and second IC detectors 112 and 113.

Here, as described above, in a state where the insertion unit side connector 21 and the first light guide side connector 41 are connected, the distal end portion 212 is inserted into the first light guide side connector 41, and the flange portion 211 abuts on the corresponding first light guide side connector 41. The flange portion 211 and the first light guide side connector 41 have a substantially cylindrical shape as a whole. Hereinafter, for convenience of description, the flange portion 211 and the first light guide side connector 41 abutting on each other are referred to as the connection portion CN (FIGS. 3 and 4).

The attachment body 111 is a portion to be attached to the connection portion CN. In the first embodiment, the attachment body 111 has a substantially cylindrical shape as a whole. In addition, the attachment body 111 is formed such that the inner diameter dimensions on one end side and the other end side are smaller than the other inner diameter dimensions and has a space SP substantially the same as the external size of the connection portion CN inside. Further, the attachment body 111 includes first and second attachment bodies 1111 and 1112 divided into a plurality of bodies (two bodies in the first embodiment) by a plane including a central axis of a cylindrical shape. The first and second attachment bodies 1111 and 1112 are fixed to each other by a fixing screw SC (FIG. 4) in a state of being combined with each other so as to fit the connection portion CN into the space SP. In this state, since the connection portion CN is fitted in the space SP, the connection between the insertion unit side connector 21 and the first light guide side connector 41 to each other is not released. That is, the attachment body 111 has an annular shape covering the periphery of the connection portion CN by combining the first and second attachment bodies 1111 and 1112 with each other.

The first IC detector 112 is used to detect connection between the attachment body 111 and the insertion unit 2 and corresponds to a first detector according to the present disclosure. As illustrated in FIG. 4, the first IC detector 112 is built in the first attachment body 1111 at a position facing the first IC tag 213 in a state where the attachment body 111 is attached to the connection portion CN. Then, the first IC detector 112 is configured with, for example, a loop antenna, transmits an electromagnetic wave serving as a power source of the first IC tag 213 by an electromagnetic induction action when energized, and also transmits an electromagnetic wave serving as a transmission command of data of the corresponding first IC tag 213. In addition, the first IC detector 112 receives data transmitted from the corresponding first IC tag 213.

The second IC detector 113 is used to detect connection between the attachment body 111 and the light guide 4 and corresponds to a second detector according to the present disclosure. As illustrated in FIG. 4, the second IC detector 113 is built in the first attachment body 1111 at a position facing the second IC tag 411 in a state where the attachment body 111 is attached to the connection portion CN. Then, the second IC detector 113 is configured with, for example, a loop antenna, transmits an electromagnetic wave serving as a power source of the second IC tag 411 by an electromagnetic induction action when energized, and also transmits an electromagnetic wave serving as a transmission command of data of the corresponding second IC tag 411. In addition, the second IC detector 113 receives data transmitted from the corresponding second IC tag 411.

Further, in the attachment body 111, as illustrated in FIG. 4, first to fourth attachment side contact points 1141 to 1144 are provided on the inner peripheral surface on the light guide 4 side.

As illustrated in FIG. 4, the first attachment side contact point 1141 is provided in the first attachment body 1111. The first attachment side contact point 1141 is electrically connected to the first one end side contact point 431 when the attachment body 111 is attached to the connection portion CN. In addition, the first attachment side contact point 1141 is electrically connected to the first IC detector 112 by a first attachment side wiring 1151 (FIG. 4) tracing the inside of the first attachment body 1111.

As illustrated in FIG. 4, the second attachment side contact point 1142 is provided in the first attachment body 1111. The second attachment side contact point 1142 is electrically connected to the second one end side contact point 432 when the attachment body 111 is attached to the connection portion CN. In addition, the second attachment side contact point 1142 is electrically connected to the second IC detector 113 by a second attachment side wiring 1152 (FIG. 4) tracing the inside of the first attachment body 1111.

As illustrated in FIG. 4, the third attachment side contact point 1143 is provided in the second attachment body 1112. The third attachment side contact point 1143 is electrically connected to the third one end side contact point 433 when the attachment body 111 is attached to the connection portion CN.

As illustrated in FIG. 4, the fourth attachment side contact point 1144 is provided in the second attachment body 1112. The fourth attachment side contact point 1144 is electrically connected to the fourth one end side contact point 434 when the attachment body 111 is attached to the connection portion CN.

The third and fourth attachment side contact points 1143 and 1144 are electrically connected to each other by assembly checking wiring 1153 (FIG. 4) tracing the inside of the second attachment body 1112.

Operation of Control Unit

Next, the lighting drive control executed by the control unit 36 described above is described.

Figure 5:
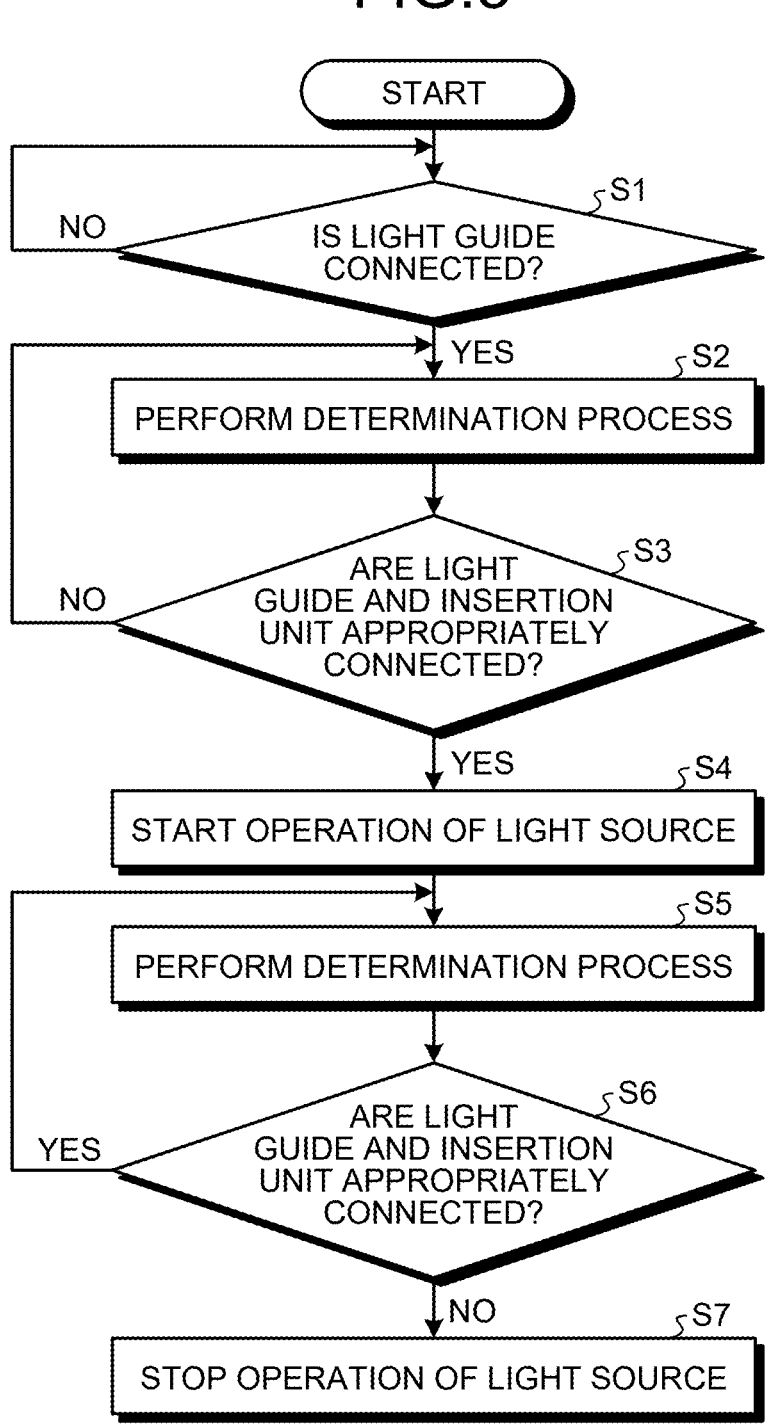
FIG. 5 is a flowchart illustrating lighting drive control executed by a control unit.

FIG. 5 is a flowchart illustrating the lighting drive control executed by the control unit 36.

First, the control unit 36 constantly monitors whether the connection of the light guide 4 (the second light guide side connector 42) to the light source device 3 (the light source device side connector 30) is detected by a detection unit (not illustrated) (Step S1).

When it is determined that the connection of the light guide 4 to the light source device 3 is detected (Step S1: Yes), the control unit 36 executes the following determination process of determining whether the light guide 4 and the insertion unit 2 are appropriately connected (Step S2).

Here, the determination process executed in Step S2 is configured with first to third determination processes.

The first determination process is as follows.

The control unit 36 determines whether a path from the third light source device side wiring 3023 to the third light source device side contact point 3013 to the third other end side contact point 443 to the third light guide side wiring 453 to the third one end side contact point 433 to the third attachment side contact point 1143 to the assembly checking wiring 1153 to the fourth attachment side contact point 1144 to the fourth one end side contact point 434 to the fourth light guide side wiring 454 to the fourth other end side contact point 444 to the fourth light source device side contact point 3014 to the fourth light source device side wiring 3024 (hereinafter, referred to as an assembly checking path) is conducted.

Here, when the first and second attachment bodies 1111 and 1112 are not assembled, that is, when the attachment body 111 is not attached to the connection portion CN, the assembly checking path described above is not conducted.

Meanwhile, when the first and second attachment bodies 1111 and 1112 are assembled, that is, when the attachment body 111 is attached to the connection portion CN, the assembly checking path described above is conducted.

Then, when the assembly checking path described above is not conducted, the control unit 36 determines "No" in the first determination process. Meanwhile, when the assembly checking path described above is conducted, the control unit 36 determines "Yes" in the first determination process.

The second determination process is as follows.

The control unit 36 energizes the first IC detector 112 by tracing a path from the first light source device side wiring 3021 to the first light source device side contact point 3011 to the first other end side contact point 441 to the first light guide side wiring 451 to the first one end side contact point 431 to the first attachment side contact point 1141 to the first attachment side wiring 1151 to the corresponding first IC detector 112 (hereinafter, referred to as a first path). Then, the first IC detector 112 receives the data of the first IC tag 213 in a non-contact manner by wireless communication using an electromagnetic induction action by being energized and outputs the corresponding data to the control unit 36 by reversely tracing the first path described above.

Here, when the insertion unit side connector 21 is not connected to the first light guide side connector 41, and the first IC tag 213 does not exist in the space SP, the control unit 36 may not acquire data of the corresponding first IC tag 213.

Meanwhile, when the insertion unit side connector 21 is connected to the first light guide side connector 41, and the first IC tag 213 exists in the space SP, the control unit 36 may acquire data of the corresponding first IC tag 213.

Then, when the data of the first IC tag 213 may not be acquired, the control unit 36 determines "No" in the second determination process. Meanwhile, when the data of the first IC tag 213 may be acquired, the control unit 36 determines "Yes" in the second determination process.

The third determination process is as follows.

The control unit 36 energizes the second IC detector 113 by tracing a path from the second light source device side wiring 3022 to the second light source device side contact point 3012 to the second other end side contact point 442 to the second light guide side wiring 452 to the second one end side contact point 432 to the second attachment side contact point 1142 to the second attachment side wiring 1152 to the corresponding second IC detector 113 (hereinafter, referred to as a second path). Then, the second IC detector 113 receives the data of the second IC tag 411 in a non-contact manner by wireless communication using an electromagnetic induction action by being energized and outputs the corresponding data to the control unit 36 by reversely tracing the second path described above.

Here, when the attachment body 111 is not attached to the connection portion CN, the control unit 36 may not acquire data of the second IC tag 411.

Meanwhile, when the attachment body 111 is attached to the connection portion CN, the control unit 36 may acquire data of the corresponding second IC tag 411.

Then, when the data of the second IC tag 411 may not be acquired, the control unit 36 determines "No" in the third determination process. Meanwhile, when the data of the second IC tag 411 may be acquired, the control unit 36 determines "Yes" in the third determination process.

As a result of the determination process (Step S2), when it is determined as "No" in any one of the first to third determination processes, it is determined that the light guide 4 and the insertion unit 2 are not appropriately connected (Step S3: No), and the control unit 36 returns to Step S2.

Meanwhile, when it is determined as "Yes" in all of the first to third determination processes as a result of the determination process (Step S2), it is determined that the light guide 4 and the insertion unit 2 are appropriately connected (Step S3: Yes), and the control unit 36 starts the operation of the light source designated by the corresponding control device 9 among the visible light source 31 and the first and second excitation light sources 32 and 33 according to the control signal output from the control device 9 (Step S4). As a result, light (at least one of normal light and first and second laser beams) is output from the corresponding light source.

After Step S4, the control unit 36 executes determination process similar to that in Step S2 (Step S5).

Here, the determination processes (Steps S2 and S5) described above are executed in a cycle less than a time reference corresponding to the class defined in the laser standard indicating "safety standard of the laser product" for the laser beams (first and second laser beams) projected from the projection end of the light guide 4. Specifically, in the first embodiment, as shown in Table 2, the class of the laser beam projected from the projection end of the light guide 4 is "Class 3R". The time reference corresponding to the corresponding "Class 3R" is 0.25 seconds. Therefore, the control unit 36 executes the determination processes (Steps S2 and S5) at a cycle of 0.2 seconds which is less than 0.25 seconds.

If it is determined as "Yes" in all of the first to third determination processes as a result of the determination process (Step S5), it is determined that the light guide 4 and the insertion unit 2 are appropriately connected (Step S6: Yes), and the control unit 36 returns to Step S5.

Meanwhile, when it is determined as "No" in any one of the first to third determination processes as a result of the determination process (Step S5), it is determined that the light guide 4 and the insertion unit 2 are not appropriately connected (Step S6: No), and the control unit 36 stops the operation of the light source, the operation being started in Step S4 (Step S7). As a result, the output of the light (at least one of the normal light and the first and second laser beams) from the corresponding light source is stopped.

According to the first embodiment described above, the following effects are exhibited.

In the medical endoscope system 1 according to the first embodiment, the detection attachment 11 includes the attachment body 111 attached to the connection portion CN, the first IC detector 112 that detects the connection between the corresponding attachment body 111 and the insertion unit 2, and the second IC detector 113 that detects the connection between the corresponding attachment body 111 and the light guide 4. In addition, the control unit 36 detects the connection state between the light guide 4 and the insertion unit 2 by using the detection attachment 11 and controls the outputs of the first and second laser beams in the first and second excitation light sources 32 and 33 based on the corresponding detection result.

Therefore, when the light guide 4 and the insertion unit 2 are not appropriately connected, such as when the corresponding light guide 4 is detached from the corresponding insertion unit 2, the output of the first and second laser beams may be stopped. That is, as a result of such a configuration, the laser beam projected from the distal end of the insertion unit 2 may be designed to satisfy the requirement defined in the laser standard indicating the "safety standard of laser products". Then, the first and second laser beams projected from the projection end of the light guide 4 may have a high light amount such as the class 3R, and as a result, the light amounts of the first and second laser beams projected from the distal end of the insertion unit 2 may be ensured.

Therefore, with the light source device 3 according to the present embodiment, it is possible to ensure the light amount of the laser beam projected to the subject while securing safety.

In the medical endoscope system 1 according to the first embodiment, the attachment body 111 is divided into a plurality of bodies, and the divided bodies are combined with each other to form an annular shape that covers the periphery of the connection portion CN.

Therefore, by attaching the attachment body 111 to the connection portion CN, it is possible to design a structure for preventing the connection state between the insertion unit side connector 21 and the first light guide side connector 41 from being released.

Furthermore, in the medical endoscope system 1 according to the first embodiment, the first and second detectors according to the present disclosure is configured with the IC detectors 112 and 113 that read data of the IC tags 213 and 411.

Therefore, the connection between the attachment body 111 and each of the insertion unit 2 and the light guide 4 may be easily detected.

In addition, in the medical endoscope system 1 according to the present embodiment, the determination processes (Steps S2 and S5) are executed at a cycle less than the time reference corresponding to the class defined in the laser standard indicating the "safety standard of the laser product" with respect to the laser beam (first and second laser beams) projected from the projection end of the light guide 4.

Therefore, when the light guide 4 is detached from the insertion unit 2, before the first and second laser beams are projected from the projection end of the corresponding light guide 4 by the corresponding time reference, it is possible to detect that the light guide 4 is detached from the insertion unit 2 and stop the output of the first and second laser beams. Therefore, safety may be sufficiently ensured.

Second Embodiment

Next, a second embodiment is described.

Hereinafter, the configurations which are the same as those of the first embodiment described above are denoted by the same reference numerals, and the detailed description thereof is omitted or simplified.

In the medical endoscope system 1 according to the first embodiment described above, the detection attachment 11 is electrically connected to the control unit 36 by wire.

On the other hand, in a medical endoscope system 1 according to the second embodiment, the detection attachment 11 is communicably connected to the control unit 36 wirelessly. That is, in the medical endoscope system 1 according to the second embodiment, the first to fourth one end side contact points 431 to 434, the first to fourth other end side contact points 441 to 444, the first to fourth light guide side wiring 451 to 454, the first to fourth light source device side contact points 3011 to 3014, and the first to fourth light source device side wiring 3021 to 3024 described in the first embodiment are not provided.

Figure 6:
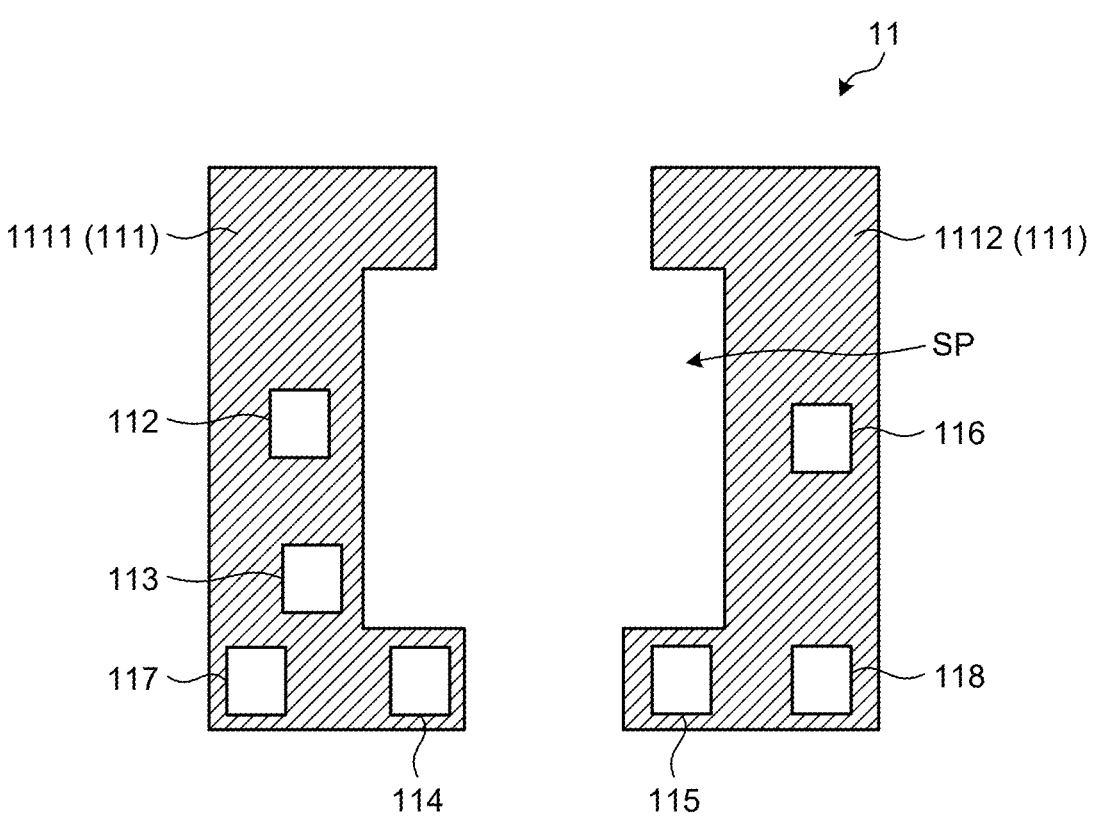
FIG. 6 is a diagram illustrating a configuration of a detection attachment according to a second embodiment.

FIG. 6 is a diagram illustrating a configuration of the detection attachment 11 according to the second embodiment.

First, a configuration of the detection attachment 11 according to the second embodiment is described.

As illustrated in FIG. 6, the detection attachment 11 according to the second embodiment includes an assembly checking IC tag 114, an assembly checking IC detector 115, a communication unit 116, and first and second batteries 117 and 118 in addition to the attachment body 111 and the first and second IC detectors 112 and 113 described in the first embodiment described above.

As illustrated in FIG. 6, the assembly checking IC tag 114 is built in the first attachment body 1111. In the second embodiment, the assembly checking IC tag 114 is configured with a known RFID tag. That is, though not specifically illustrated, the assembly checking IC tag 114 includes an antenna and an IC chip. Then, the IC chip operates by using radio waves received from the assembly checking IC detector 115 via the corresponding antenna as a power source and transmits data recorded in the IC chip to the assembly checking IC detector 115 via the corresponding antenna.

As illustrated in FIG. 6, the assembly checking IC detector 115 is built in the second attachment body 1112 at a position facing the assembly checking IC tag 114 in a state where the attachment body 111 is assembled. Then, the assembly checking IC detector 115 is configured with, for example, a loop antenna, transmits an electromagnetic wave serving as a power source of the assembly checking IC tag 114 by an electromagnetic induction action when energized, and also transmits an electromagnetic wave serving as a transmission command of data of the corresponding assembly checking IC tag 114. The assembly checking IC detector 115 receives data transmitted from the corresponding assembly checking IC tag 114.

The communication unit 116 is connected to the light source device 3 according to the second embodiment so as to be able to wirelessly transmit and receive data.

As illustrated in FIG. 6, the first battery 117 is built in the first attachment body 1111. Also, the first battery 117 supplies power to the first and second IC detectors 112 and 113 under the control of the control unit 36.

As illustrated in FIG. 6, the second battery 118 is built in the second attachment body 1112. Then, the second battery 118 supplies power to the assembly checking IC detector 115 and the communication unit 116 under the control of the control unit 36.

Figure 7:
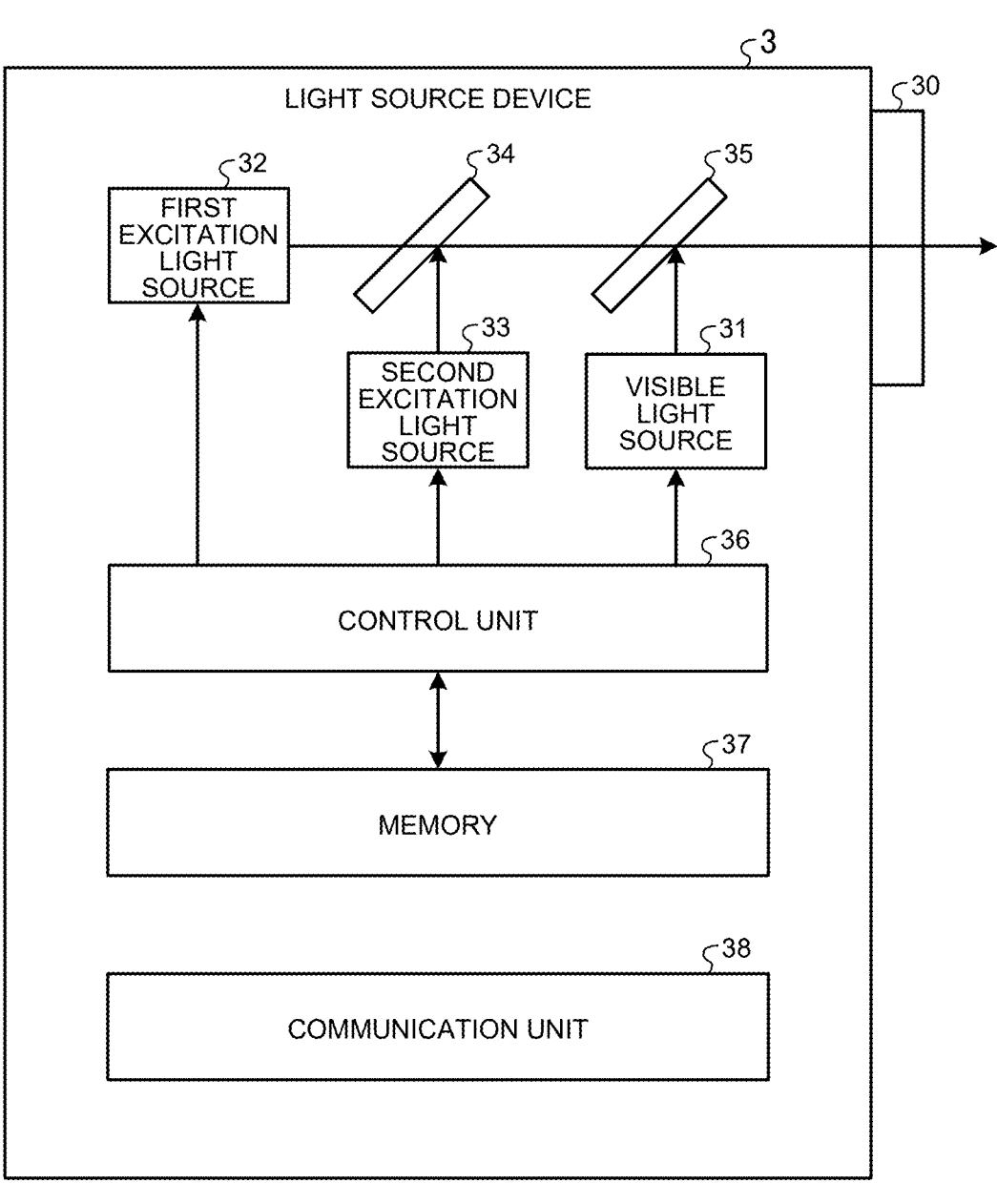
FIG. 7 is a block diagram illustrating a configuration of a light source device according to the second exemplary embodiment.

FIG. 7 is a block diagram illustrating a configuration of the light source device 3 according to the second embodiment.

In the light source device 3 according to the second embodiment, as illustrated in FIG. 7, a communication unit 38 is added to the light source device 3 described in the first embodiment described above.

The communication unit 38 is connected to the communication unit 116 in the detection attachment 11 so as to be able to wirelessly transmit and receive data.

Then, in Steps S2 and S5 described in the first embodiment described above, the control unit 36 according to the present second embodiment executes the following determination processes (the first to third determination processes).

The first determination process is as follows.

The control unit 36 transmits a control signal to the second battery 118 via the communication units 38 and 116. As a result, the second battery 118 energizes the assembly checking IC detector 115. Then, the assembly checking IC detector 115 receives data of the assembly checking IC tag 114 in a non-contact manner by wireless communication using the electromagnetic induction action when being energized. Furthermore, the corresponding data is transmitted to the control unit 36 via the communication units 116 and 38.

Here, when the first and second attachment bodies 1111 and 1112 are not assembled, that is, when the attachment body 111 is not attached to the connection portion CN, the control unit 36 may not receive the data of the assembly checking IC tag 114.

On the other hand, when the first and second attachment bodies 1111 and 1112 are assembled, that is, the attachment body 111 is attached to the connection portion CN, the control unit 36 may acquire the data of the assembly checking IC tag 114.

Then, when the data of the assembly checking IC tag 114 may not be acquired, the control unit 36 determines "No" in the first determination process. Meanwhile, when the data of the assembly checking IC tag 114 may be acquired, the control unit 36 determines "Yes" in the first determination process.

The second determination process is as follows.

The control unit 36 transmits a control signal to the first battery 117 via the communication units 38 and 116. As a result, the first battery 117 energizes the first IC detector 112. Then, the first IC detector 112 receives the data of the first IC tag 213 in a non-contact manner by the wireless communication using an electromagnetic induction action when being energized. Furthermore, the corresponding data is transmitted to the control unit 36 via the communication units 116 and 38.

Here, when the insertion unit side connector 21 is not connected to the first light guide side connector 41, and the first IC tag 213 does not exist in the space SP, the control unit 36 may not acquire data of the corresponding first IC tag 213.

Meanwhile, when the insertion unit side connector 21 is connected to the first light guide side connector 41, and the first IC tag 213 exists in the space SP, the control unit 36 may acquire data of the corresponding first IC tag 213.

Then, when the data of the first IC tag 213 may not be acquired, the control unit 36 determines "No" in the second determination process. Meanwhile, when the data of the first IC tag 213 may be acquired, the control unit 36 determines "Yes" in the second determination process.

The third determination process is as follows.

The control unit 36 transmits a control signal to the first battery 117 via the communication units 38 and 116. As a result, the first battery 117 energizes the second IC detector 113. Then, the second IC detector 113 receives the data of the second IC tag 411 in a non-contact manner by the wireless communication using an electromagnetic induction action when being energized. Furthermore, the corresponding data is transmitted to the control unit 36 via the communication units 116 and 38.

Here, when the attachment body 111 is not attached to the connection portion CN, the control unit 36 may not acquire data of the second IC tag 411.

Meanwhile, when the attachment body 111 is attached to the connection portion CN, the control unit 36 may acquire data of the corresponding second IC tag 411.

Then, when the data of the second IC tag 411 may not be acquired, the control unit 36 determines "No" in the third determination process. Meanwhile, when the data of the second IC tag 411 may be acquired, the control unit 36 determines "Yes" in the third determination process.

Even in the case of being configured as in the second embodiment described above, the same effects as those of the first embodiment described above are exhibited.

Other Embodiments

Although the embodiments for carrying out the present disclosure have been described so far, the present disclosure should not be limited only to the first and second embodiments described above.

In the first and second embodiments described above, the first IC tag 213 is provided in the insertion unit side connector 21, the second IC tag 411 is provided in the first light guide side connector 41, and the first and second IC detectors 112 and 113 are provided in the attachment body 111, but the present disclosure is not limited thereto. For example, if power supply to the first and second IC detectors 112 and 113 is devised, the corresponding first and second IC detectors 112 and 113 may be provided in the insertion unit side connector 21 and the first light guide side connector 41, respectively, and the first and second IC tags 213 and 411 may be provided in the attachment body 111.

In the first and second embodiments described above, the combination of the IC tag and the IC detector is employed as the configuration for detecting the connection between the attachment body 111 and each of the insertion unit 2 and the light guide 4, but the present disclosure is not limited thereto. As the corresponding configuration, a combination of a magnet and a Hall element may be employed. At this time, any one of the magnet and the Hall element corresponds to the first and second detectors according to the present disclosure.

In the first and second embodiments described above, the laser beam source device according to the present disclosure includes two of the first and second excitation light sources 32 and 33, but the present disclosure is not limited thereto. The number of the laser beam source devices according to the present disclosure is not limited to two, and may be one or may be three or more.

In the first and second embodiments described above, in Step S7, the control unit 36 stops the operation of the light source that starts the operation in Step S4, but the present disclosure is not limited thereto, and the light amount may be configured to be reduced to a light amount that may ensure safety without stopping outputting of the light.

In the first and second embodiments described above, when only normal light is projected from the visible light source 31, the corresponding normal light is different from laser beam that needs to be considered for safety, and thus the lighting drive control described above may not be executed. That is, after it is determined that the connection of the light guide 4 to the light source device 3 is detected (Step S1: Yes), the control unit 36 may start the operation of the visible light source 31 in Step S4 without executing the determination process (Step S2) or the like.

In addition, in the first and second embodiments described above, when the normal light and at least one of the first and second laser beams are simultaneously projected, only the output of the corresponding laser beam may be stopped in Step S7.

In at least one of the case of determining "No" in Step S3 and the case of determining "No" in Step S6 in the first and second embodiments described above, the control unit 36 may cause an external notification unit to notify warning information indicating that the light guide 4 and the insertion unit 2 are not appropriately connected. For example, the control unit 36 causes the display device 7 as a notification unit to display the corresponding warning information via the control device 9. The corresponding notification unit is not limited to the display device 7, and other display devices, a speaker that outputs the warning information by voice, or the like may be employed.

Then, a user such as a doctor may recognize that the light guide 4 and the insertion unit 2 are not appropriately connected by recognizing the corresponding warning information. Therefore, convenience may be improved.

In the embodiments described above, the first to third determination processes are executed as the determination processes (Steps S2 and S5), but the present disclosure is not limited thereto, and only the second and third determination processes may be executed. That is, in Steps S3 and S6, as a result of the determination processes (Steps S2 and S5), the control unit 36 determines that the light guide 4 and the insertion unit 2 are not appropriately connected (Steps S3 and S6: No), when it is determined as "No" in either the second or third determination process, and determines that the light guide 4 and the insertion unit 2 are appropriately connected (Steps S3 and S6: Yes), when it is determined as "Yes" in both the second and third determination processes.

Note that the following configurations also belong to the technical scope of the present disclosure.

(1) A medical detection attachment including: an attachment body attached to a connection portion between a light guide configured to guide a laser beam and a rigid endoscope configured to irradiate a subject with the laser beam via the light guide; a first detector provided in the attachment body and configured to detect connection between the attachment body and the rigid endoscope; and a second detector provided in the attachment body and configured to detect connection between the attachment body and the light guide.

(2) The medical detection attachment according to (1), wherein the attachment body is divided into a plurality of bodies such that the divided bodies are combined with each other to form an annular shape that covers the periphery of the connection portion.

(3) The medical detection attachment according to (1) or (2), wherein the rigid endoscope includes one of a first IC tag and a first IC detector configured to read data of the first IC tag in a non-contact manner by wireless communication using an electromagnetic induction action with the first IC tag, the first detector is another one of the first IC tag and the first IC detector, the light guide includes one of a second IC tag and a second IC detector configured to read data of the second IC tag in a non-contact manner by wireless communication using an electromagnetic induction action with the second IC tag, and the second detector is another one of the second IC tag and the second IC detector.

(4) A medical endoscope system including: a laser beam source device configured to project a laser beam; a light guide configured to guide the laser beam; a rigid endoscope configured to irradiate a subject with the laser beam via the light guide; a medical detection attachment configured to detect a connection state between the light guide and the rigid endoscope; and a light source control device configured to detect a connection state between the light guide and the rigid endoscope by using the medical detection attachment, and control output of the laser beam in the laser beam source device based on the corresponding detection result, wherein the medical detection attachment includes an attachment body attached to a connection portion between the light guide and the rigid endoscope, a first detector provided in the attachment body and configured to detect connection between the attachment body and the rigid endoscope, and a second detector provided in the attachment body and configured to detect connection between the attachment body and the light guide.

(5) The medical endoscope system according to (4), wherein the rigid endoscope includes a first IC tag, the first detector is a first IC detector configured to read data of the first IC tag in a non-contact manner by wireless communication using an electromagnetic induction action with the first IC tag, the light guide includes a second IC tag, the second detector is a second IC detector configured to read data of the second IC tag in a non-contact manner by wireless communication using an electromagnetic induction action with the second IC tag, and the light source control device is electrically connected to each of the first IC detector and the second IC detector, and configured to drive each of the first IC detector and the second IC detector, and read data of the first IC tag and data of the second IC tag to detect connection of the attachment body to each of the rigid endoscope and the light guide.

(6) The medical endoscope system according to (4), wherein the rigid endoscope includes a first IC tag, the first detector is a first IC detector configured to read data of the first IC tag in a non-contact manner by wireless communication using an electromagnetic induction action with the first IC tag, the light guide includes a second IC tag, the second detector is a second IC detector configured to read data of the second IC tag in a non-contact manner by wireless communication using an electromagnetic induction action with the second IC tag, the attachment body is further includes: a communication unit configured to wirelessly transmit the data of the first IC tag read by the first IC detector and the data of the second IC tag read by the second IC detector; and a battery configured to supply power to the first IC detector, the second IC detector, and the communication unit, and the light source control device is configured to detect connection between the attachment body and each of the rigid endoscope and the light guide based on the data of the first IC tag and the data of the second IC tag wirelessly transmitted from the communication unit.

(7) The medical endoscope system according to any one of (4) to (6), wherein the light source control device is configured to detect a connection state between the light guide and the rigid endoscope by using the medical detection attachment in a period less than a time reference corresponding to a class defined in a laser standard indicating a safety standard of a laser product with respect to the laser beam that is projected from the laser beam source device and then projected from the light guide.

With the medical detection attachment and the medical endoscope system according to the present disclosure, it is possible to secure the light amount of the laser beam projected to the subject while ensuring safety.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical detection attachment comprising:
   an attachment body attached to a connection portion connecting a light guide configured to guide a laser beam and an endoscope configured to irradiate a subject with the laser beam via the light guide;
   a first detector provided in the attachment body and configured to detect connection between the attachment body and the endoscope; and
   a second detector provided in the attachment body and configured to detect connection between the attachment body and the light guide, wherein each of the first detector and the second detector include one of Hall effect element, an integrated circuit (IC) detector, or an IC tag.

2. The medical detection attachment according to claim 1, wherein the attachment body includes a plurality of bodies configured to be combined with each other to form an annular shape that covers the periphery of the connection portion.

3. The medical detection attachment according to claim 2, further comprising a safety circuit configured to prevent the laser beam from being projected if the plurality of bodies are not fully combined to form the annular shape.

4. The medical detection attachment according to claim 2, further comprising:
   an assembly detector configured to detect that the plurality of bodies are combined with each other, wherein the assembly detector includes an assembly checking wiring electrically connecting the plurality of bodies, or a combination of an assembly checking IC tag and an assembly checking IC detector provided in the plurality of bodies.

5. The medical detection attachment according to claim 1, wherein the endoscope includes one of a first IC tag and a first IC detector configured to read data of the first IC tag in a non-contact manner by wireless communication using an electromagnetic induction action with the first IC tag,
   the first detector is another one of the first IC tag and the first IC detector,
   the light guide includes one of a second IC tag and a second IC detector configured to read data of the second IC tag in a non-contact manner by wireless communication using an electromagnetic induction action with the second IC tag, and
   the second detector is another one of the second IC tag and the second IC detector.

6. The medical detection attachment according to claim 1, wherein the endoscope is a rigid endoscope.

7. The medical detection attachment according to claim 1, wherein the endoscope includes a first magnet, and the first detector is a first Hall effect element configured to detect the presence of the first magnet; and the light guide includes a second magnet, and the second detector is a second Hall effect element configured to detect the presence of the second magnet.

8. A medical endoscope system comprising:

a laser beam source device configured to project a laser beam;

a light guide configured to guide the laser beam;

an endoscope configured to irradiate a subject with the laser beam via the light guide;

a medical detection attachment configured to detect a connection state between the light guide and the endoscope; and a light source control device configured to detect a connection state between the light guide and the endoscope by using the medical detection attachment, and control output of the laser beam in the laser beam source device based on the corresponding detection result, wherein the medical detection attachment includes an attachment body attached to a connection portion connecting the light guide and the endoscope, a first detector provided in the attachment body and configured to detect connection between the attachment body and the endoscope, and a second detector provided in the attachment body and configured to detect connection between the attachment body and the light guide, wherein each of the first detector and the second detector include one of Hall effect element an integrated circuit (IC) detector, or an IC tag.

9. The medical endoscope system according to claim 8, wherein the endoscope includes a first IC tag, the first detector is a first IC detector configured to read data of the first IC tag in a non-contact manner by wireless communication using an electromagnetic induction action with the first IC tag, the light guide includes a second IC tag, the second detector is a second IC detector configured to read data of the second IC tag in a non-contact manner by wireless communication using an electromagnetic induction action with the second IC tag, and the light source control device is electrically connected to each of the first IC detector and the second IC detector, and configured to drive each of the first IC detector and the second IC detector, and read data of the first IC tag and data of the second IC tag to detect connection of the attachment body to each of the endoscope and the light guide.

10. The medical endoscope system according to claim 8, wherein the endoscope includes a first IC tag, the first detector is a first IC detector configured to read data of the first IC tag in a non-contact manner by wireless communication using an electromagnetic induction action with the first IC tag, the light guide includes a second IC tag, the second detector is a second IC detector configured to read data of the second IC tag in a non-contact manner by wireless communication using an electromagnetic induction action with the second IC tag, the attachment body further includes:

a communication circuit configured to wirelessly transmit the data of the first IC tag read by the first IC detector and the data of the second IC tag read by the second IC detector; and a battery configured to supply power to the first IC detector, the second IC detector, and the communication circuit, and the light source control device is configured to detect connection between the attachment body and each of the endoscope and the light guide based on the data of the first IC tag and the data of the second IC tag wirelessly transmitted from the communication circuit.

11. The medical endoscope system according to claim 8, wherein the light source control device is configured to detect a connection state between the light guide and the endoscope by using the medical detection attachment in a period less than a time reference corresponding to a class defined in a laser standard indicating a safety standard of a laser product with respect to the laser beam that is projected from the laser beam source device and then projected from the light guide, wherein the time reference is based on the maximum permissible exposure (MPE) or the accessible emission limit (AEL) for the specified class of the laser beam.

12. The medical endoscope system according to claim 8, wherein the endoscope is a rigid endoscope.

13. The medical endoscope system according to claim 8, wherein the endoscope includes a first magnet, and the first detector is a first Hall effect element configured to detect the presence of the first magnet; and the light guide includes a second magnet, and the second detector is a second Hall effect element configured to detect the presence of the second magnet.

14. The medical endoscope system according to claim 8, wherein the first detector and the second detector are IC detectors configured to wirelessly read data from respective IC tags associated with the endoscope and the light guide.

* * * * *